United States Patent [19]
Wu

[11] Patent Number: 5,902,898
[45] Date of Patent: May 11, 1999

[54] PREPARATION OF ARALKANOIC ACIDS AND ESTERS USING MIXED LIGAND CATALYST

[75] Inventor: Tse-Chong Wu, Baton Rouge, La.

[73] Assignee: Albemarle Corporation, Richmond, Va.

[21] Appl. No.: 08/952,944

[22] PCT Filed: May 23, 1995

[86] PCT No.: PCT/US95/06459

§ 371 Date: Feb. 26, 1998

§ 102(e) Date: Feb. 26, 1998

[87] PCT Pub. No.: WO96/37453

PCT Pub. Date: Nov. 28, 1996

Related U.S. Application Data

[63] Continuation-in-part of application No. 08/186,933, Jan. 27, 1994, Pat. No. 5,482,596.

[51] Int. Cl.$^6$ ..................................................... C07C 51/10
[52] U.S. Cl. .............................................. 562/406; 560/56
[58] Field of Search .................................................. 560/56

[56] References Cited

PUBLICATIONS

Samsel et al J. Am. Chem. Soc. 107, 7606–7617 (1985).
Irie et al Synlett, Apr. 1991 265–266.

*Primary Examiner*—Paul J. Killos
*Attorney, Agent, or Firm*—Philip M. Pippenger

[57] ABSTRACT

The activity of a palladium catalyst in the carboxylation of an aralkene with carbon monoxide and water or an alcohol in the absence of oxygen can be enhanced when it is used in conjunction with (A) a ligand mixture comprising compounds corresponding to the formulas $R_3ZY$ and $R'_3Z$ wherein each R and R' is independently selected from alkyl, aryl and substituted aryl groups; Y is a member of Group VIA of the Periodic Table; and Z is an element having a Pauling electronegativity of 1.9–2.5 or (B) a complex ligand providing all of the elements of said mixture. The invention has particular utility in carboxylating an aralkene such as 4-isobutylstyrene or 2-methoxy-6-vinylnaphthalene to ibuprofen or naproxen or their esters; and the preferred novel ligand is usually a 50/50 mixture of phosphine and phosphine oxide.

9 Claims, No Drawings

PREPARATION OF ARALKANOIC ACIDS AND ESTERS USING MIXED LIGAND CATALYST

This application is a continuation-in-part of application Ser. No. 186,933, filed Jan. 27, 1994, now U.S. Pat. No. 5,482,596.

FIELD OF THE INVENTION

The invention relates to a process for preparing aralkanoic acids and, more particularly, relates to such a process employing a novel catalyst system.

BACKGROUND

As disclosed, e.g., in U.S. Pat. No. 4,694,100 (Shimizu et al.) and British Patent 1,565,235 (Mitsubishi), it is known that aralkenes, such as 4-isobutylstyrene, can be carboxylated with carbon monoxide and water or an alcohol in the presence of a palladium catalyst under acidic conditions to form an aralkanoic acid or ester, such as ibuprofen. Alper et al., *J. Chem. Soc. Chem. Comm.*, 1983, pp. 1270–1271, disclose a similar reaction employing a mixture of palladium and copper and requiring the presence of oxygen; and European Patent Application 284,310 (Hoechst Celanese) teaches the use of a palladium catalyst in association with a phosphine ligand to accomplish the carboxylation of 1-(4-isobutylphenyl)ethanol to ibuprofen with carbon monoxide in an aqueous acidic medium.

These known processes have been used with some success. However, it would be desirable to develop a process that would not require the presence of oxygen or an acidic medium or the use of an uneconomical starting material like 1-(4-isobutylphenyl)ethanol but would still provide the acid or ester product in good yield.

SUMMARY OF THE INVENTION

It has been found that the activity of a palladium catalyst in the carboxylation of an aralkene with carbon monoxide and water or an alcohol in the absence of oxygen can be enhanced when it is used in conjunction with (A) a ligand mixture comprising compounds corresponding to the formulas $R_3ZY$ and $R'_3Z$ wherein each R and R' is independently selected from alkyl, aryl, and substituted aryl groups; Y is a member of Group VIA of the Periodic Table; and Z is an element having a Pauling electronegativity of 1.9–2.5 or (B) a complex ligand providing all of the elements of said mixture.

Thus, in the process of the invention, an aralkanoic acid or ester corresponding to the formula $CH(R^3)(R^4)$—$C(R^2)(Ar)$—$COOR^1$ is prepared by treating an aralkene having the formula $C(R^3)(R^4)$=$C(R^2)Ar$ and a compound of the formula $R^1OH$ with carbon monoxide at a temperature of 25–200° C. and a pressure of at least ~1 atmosphere (~0.1 MPa) in the absence of oxygen and in the presence of a palladium catalyst mixture containing a combination of $R_3ZY$ and $R'_3Z$ ligand elements;

R and R' in the above formulas being independently selected from alkyl, aryl, and substituted aryl groups; Y being a member of Group VIA of the Periodic Table; Z being an element having a Pauling electronegativity of 1.9–2.5; $R^1$ being hydrogen or alkyl; $R^2$, $R^3$, and $R^4$ being independently selected from hydrogen, alkyl, halo, trifluoromethyl, alkoxy, alkylthio, alkanoyl, cycloalkyl-substituted alkyl, cycloalkyl, substituted or unsubstituted aryl or heteroaryl, and substituted or unsubstituted aroyl or heteroarylcarbonyl groups; and Ar being substituted or unsubstituted aryl.

DETAILED DESCRIPTION

Aralkenes that may be carboxylated in the practice of the invention may be any of those indicated above.

Alkyl substituents in these compounds may have straight or branched chains and contain 1–20 carbons, such as methyl, ethyl, propyl, butyl, isobutyl, sec-butyl, t-butyl, pentyl, hexyl, octyl, 2-ethylhexyl, 1,1,3,3-tetramethylbutyl, decyl, tetradecyl, eicosyl, etc., while cycloalkyl groups contain 3–7 carbons (e.g., cyclopropyl, cyclobutyl, cyclopentyl, cyclohexyl, and cycloheptyl), and cycloalkyl-substituted alkyl groups have a cycloalkyl moiety of 3–7 carbons and a straight- or branched-chain alkyl moiety of 1–8 carbons, as in cyclopropylmethyl, cyclobutylmethyl, cycloheptylmethyl, 2-cyclopropylethyl, 2-cyclohexylethyl, 3-cyclopentylpropyl, 4-cyclopropylbutyl, 6-cyclohexylhexyl, and the like. When present, alkoxy and alkylthio substituents may be straight- or branched-chain groups containing 1–10 carbons (e.g., methoxy, ethoxy, propoxy, isopropoxy, butoxy, sec-butoxy, t-butoxy, hexyloxy, octyloxy, decyloxy, methylthio, ethylthio, propylthio, butylthio, pentylthio, hexylthio, octylthio, etc.); and any alkanoyl groups have 2–18 carbons, as in acetyl, propionyl, butyryl, isobutyryl, pivalolyl, valeryl, hexanoyl, octanoyl, lauroyl, and stearoyl groups, etc.

Both the essential aryl substituent and any optional aryl substituents in the aralkenes may be phenyl or naphthyl groups that are unsubstituted or that bear one or more substituents selected from halo (chloro, bromo, fluoro, or iodo), amino, nitro, hydroxy, alkyl, alkoxy, aryloxy (including phenoxy and phenoxy substituted with halo, alkyl, alkoxy, and the like), and haloalkyl having a straight or branched chain of 1–8 carbons bearing at least one halo substituent (including, e.g., chloromethyl, bromomethyl, fluoromethyl, iodomethyl, 2-chloroethyl, 3-bromopropyl, 4-fluorobutyl, dichloromethyl, dibromomethyl, 2,2-difluoroethyl, 3,3-dichloropropyl, 4,4-dichlorobutyl, trichloromethyl, trifluoromethyl, 2,2,2-trifluoroethyl, 2,3,3-trifluoropropyl, 1,1,2,2-tetrafluoroethyl, etc.). Any aroyl substitutents in the aralkenes are aroyl groups corresponding to the above aryl groups, i.e., benzoyl or naphthoyl groups that are unsubstituted or that bear one or more of the substituents listed above.

When the aralkene includes a substituted or unsubstituted heteroaryl group, that group has a 5–10 membered mono- or fused-heteroaromatic ring containing at least one heteroatom selected from nitrogen, oxygen, and sulfur (e.g., 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl, indolyl, etc.) and may bear one or more substituents selected from halo, amino, nitro, hydroxy, alkyl, alkoxy, and haloalkyl on the ring. Any heteroarylcarbonyl substitutents in the aralkenes are heteroarylcarbonyl groups corresponding to the above heteroaryl groups, e.g., furoyl, thienoyl, nicotinoyl, isonicotinoyl, pyrazolylcarbonyl, imidazolylcarbonyl, pyrimidinylcarbonyl, and benzimidazolylcarbonyl groups that are unsubstituted or that bear one or more of the substituents listed above.

The preferred aralkene starting materials are compounds in which Ar is substituted or unsubstituted aryl; and $R^2$, $R^3$, and $R^4$ represent hydrogen, $C_1$–$C_2$ alkyl, trifluoromethyl, or substituted or unsubstituted phenyl. More preferably, Ar is alkylphenyl or alkoxynaphthyl; and $R^2$, $R^3$, and $R^4$ are hydrogen, methyl, or trifluoromethyl.

The $R^1OH$ hydroxyl compound with which the aralkene is reacted is ordinarily water or an alkanol in which $R^1$ represents a linear or branched chain of 1–8 carbons, as in methanol, ethanol, propanol, isopropyl alcohol, n-, iso-, sec-, and t-butyl alcohols, the pentanols, the hexanols, the octanols, etc.—methanol and ethanol, especially ethanol, being preferred when an ester product is sought. However, other alcohols, glycols, aromatic hydroxy compounds, and other sources of alkoxy ions [e.g., compounds corresponding to the formulas $HC(OR^1)_3$, $R^5_2C(OR^1)_2$, $HCOOR^1$, $B(OR^1)_3$, $Ti(OR^1)_4$, and $Al(OR^1)_3$, wherein $R^1$ is as previously defined and $R^5$ is hydrogen or any of the groups defined by $R^1$] can be used as alternatives to these alkanols if desired.

The amount of $R^1$ OH employed in the reaction should be at least ~1 mol per mol of aralkene, and it is usually preferred to use an excess of the hydroxyl compound to assist in driving the reaction to completion. In fact, the hydroxyl compound can be used in as high an amount as the size of the reaction vessel permits, and particularly large amounts are apt to be desirable to serve the additional function of reaction medium when no other reaction medium is utilized. However, controlling the amount of hydroxyl compound is advantageous in producing the highest yields of product, so it is normally preferred to employ ~2–50, more preferably ~3–24, mols of hydroxyl compound per mol of aralkene reactant.

As already indicated, the amount of carbon monoxide used in the process of the invention should be enough to provide a partial pressure of at least ~1 atmosphere (~0.1 MPa) in the reaction vessel, and higher pressures up to the pressure limits of the reaction vessel can be utilized. Pressures up to ~3000 psig (~20.7 MPa) are convenient to employ. Preferably, the pressure is ~100–3000 psig (~0.7–20.7 MPa), more preferably ~200–800 psig (~1.4–5.5 MPa). Since the presence of oxygen is undesirable in the practice of the invention, it is most preferable to conduct the reaction in an atmosphere of 100% carbon monoxide. However, part of this atmosphere can be replaced by one or more inert gases, such as nitrogen, argon, etc., as long as the reaction is not slowed to the point of necessitating exceptionally long periods for completing the reaction.

The process of the invention is usually conducted at a temperature of 25–200° C., preferably 25–120° C., and most preferably 50–100° C., although higher temperatures can also be used. A small advantage in yield can be obtained by gradually increasing the temperature within the preferred ranges during the course of the reaction.

As already indicated, an acidic medium is not required for the process of the invention, and it is sometimes preferred to conduct the reaction in the absence of any added acid. However, acid may be added in gaseous or liquid form when its presence is desired. When added acid is utilized, it may be an acid such as sulfuric, phosphoric, or sulfonic acid but is preferably a hydrogen halide, especially hydrogen chloride or hydrogen bromide; and it is usually employed in an amount such as to provide up to 40 mols, preferably up to 10 mols, and more preferably up to ~4 mols of $H^+$ per mol of aralkene reactant.

In the processes conducted to form ester products, it can be important to add any acid in gaseous or other non-aqueous form (e.g., as an alcoholic solution) when it is desired to maintain anhydrous conditions in order to avoid the formation of an acid by-product. However, in the syntheses of acid products, as well as in the ester syntheses when some contamination with acid by-products is tolerable, an acid added to the reaction mixture may alternatively be incorporated in the form of an aqueous solution, e.g., the common hydrochloric and hydrobromic acid solutions. Hydrochloric acid is frequently preferred, especially hydrochloric acid having a concentration of ~10–30%.

Except for its ligand component, the palladium catalyst system of the invention is conventional. Thus, it comprises a reaction-promoting quantity of palladium metal and/or a palladium salt (e.g., palladium(II) chloride, bromide, nitrate, sulfate, or acetate), optionally in conjunction with one or more copper salts (such as copper(II) chloride, bromide, nitrate, sulfate, or acetate), as well as the inventive combination of $R_3ZY$ and $R'_3Z$ ligand elements; and the palladium component(s) and any copper component(s) may be unsupported or supported on, e.g., carbon, silica, alumina, zeolite, clay, or a polymeric material to provide a heterogeneous catalyst.

The novel ligand component of the catalyst system is a combination of $R_3ZY$ and $R'_3Z$ ligand elements wherein Z is an element having a Pauling electronegativity of 1.9–2.5 (e.g., sulfur, nitrogen, osmium, phosphorus, arsenic, antimony, mercury, tellurium, germanium, or bismuth), Y is a member of Group VIA of the Periodic Table (usually oxygen, sulfur, or selenium), and each R and R' is independently selected from alkyl, aryl, and substituted aryl groups or is joined together with the other Rs or R's and Z to form a heteroaromatic ring, e.g., pyridine, thiopyran, etc.

It is frequently preferred for each of the Rs and R's to be separate and identical $C_1$–$C_6$ alkyl, phenyl, or substituted phenyl groups (most preferably phenyl) and Z to be phosphorus. Also, although the combination of $R_3ZY$ and $R'_3Z$ ligand elements can be provided by using a single compound combining those elements (e.g., 1,3-bis(diphenylphosphino) propane monoxide, which has the required $R_3Z$, $R'_3Z$, and Z-Y), it is usually preferred for the ligand to be a mixture of separate $R_3ZY$ and $R'_3Z$ compounds, such as triphenylphosphine oxide/triphenyl phosphine, cyclohexyldiphenylphosphine oxide/cyclohexyldiphenylphosphine, triphenylphosphineoxide/cyclohexyldiphenylphosphine, and ethyldiphenylphosphine oxide/ethyldiphenylphosphine mixtures, etc. When a ligand mixture is used, the $R_3ZY/R'_3Z$ ratio may vary from 1/99 to 99/1. However, it is preferably in the range of 80/20 to 20/80, more preferably 60/40 to 40/60; and it is most preferable for the ligand mixture to be composed of substantially equal parts of the two ligands.

The ligand component of the catalyst mixture is used in an amount such as to provide at least one mol, preferably ~2–40 mols, and more preferably 2–20 mols of ligand per mol of the palladium and any copper components. The amount of palladium and optional copper components is preferably such as to provide ~4–8000, more preferably ~10–4000, and most preferably ~20–2000 mols of aralkene reactant per mol of these metal components.

Although some or all of the components of the catalyst mixture can be premixed before they are added to the reaction vessel, it is usually preferred to add the components (e.g., palladium(II) chloride, copper(II) chloride, and a ligand mixture of triphenylphosphine and triphenylphosphine oxide) individually, either simultaneously or sequentially.

It is not necessary to employ a solvent in the process of the invention, since an excess of the hydroxyl reactant can be used to serve as a reaction medium. However, it is sometimes desirable to employ one or more solvents such as an alcohol different from the hydroxyl reactant (e.g., methanol, ethanol, a propanol, a butanol, a hexanol, etc.); an acid or ester, such as formic or acetic acid or ethyl acetate; an aromatic hydrocarbon, such as toluene, ethylbenzene, xylenes, and the like; a ketone, such as acetone, methyl ethyl ketone, diethyl ketone, methyl n-propyl ketone, acetophenone, etc.; or a linear, poly, or cyclic ether, such as diethyl ether, di-n-propyl ether, di-n-butyl ether, ethyl n-propyl ether, glyme (the dimethyl ether of ethylene glycol), diglyme (the dimethyl ether of diethylene glycol), tetrahydrofuran, dioxane, 1,3-dioxolane, etc.

Since some of these solvents (e.g., the alcohols, acids, and esters) are reactive in the process, they should be employed only when the by-product formation consequent from their use can be tolerated. Thus, the solvents which are at least relatively inert under the reaction conditions are apt to be preferred. Ketones such as methyl ethyl ketone are generally preferred when it is important to minimize by-product formation, although ethers, especially tetrahydrofuran, can be used with satisfactory results, particularly when the process is not conducted under acidic conditions.

When employed, the solvent may be used in an amount up to ~100 mL per gram of aralkene reactant. However, the process is most advantageously conducted in the presence of ~1–30 mL of solvent per gram of aralkene.

The process of the invention leads to the formation of an acid (such as ibuprofen or naproxen when the aralkene is, respectively, 4-isobutylstyrene or 2-methoxy-6-vinylnaphthalene) when the hydroxyl reactant is water, an ester when the aralkene is reacted with an alcohol under anhydrous conditions, or a mixture of acid and ester when both water and an alcohol are used together with the aralkene. When an ester is formed by the process, it canbe conveniently converted to the acid by conventional hydrolysis techniques.

The following examples are given to illustrate the invention and are not intended as a limitation thereof. Abbreviations used therein and possibly needing definition are shown in the table below.

| Definitions Table | |
|---|---|
| Me | methyl |
| Et | ethyl |
| Cy | cyclohexyl |
| Ph | phenyl |
| MEK | methyl ethyl ketone |
| THF | tetrahydrofuran |
| GC | gas chromatography |

EXAMPLE 1

Part A (Comparative)

Charge a 100-mL Hastelloy B autoclave with 0.029 g (0.16 mmol) of $PdCl_2$ and 0. 13 g (0.50 mmol) of triphenylphosphine. Purge the autoclave three times with 500 psig (3.45 MPa) of CO, and add a solution of 1.28 g (8.0 mmol) of 4-isobutylstyrene, 1.0 mL of water, and 30 mL of THF. Purge the autoclave two more times with 500 psig (3.45 MPa) of CO, and then fill it with CO so as to provide a pressure of 500 psig (3.45 MPa). Agitate the mixture at 50° C. and monitor the reaction by GC periodically. The results of the analyses are shown in Table I.

Part B (Comparative)

Essentially repeat Part A except for replacing the triphenylphosphine with 0. 15 g (0.54 mmol) of triphenylphosphine oxide. After 24 hours at 50° C., GC analyses show that no reaction has occurred.

Part C

Essentially repeat Part A except for replacing the triphenylphosphine with 0. 14 g (0.53 mmol) of $Ph_3P/Ph_3PO$ (85/15). The reaction results in the formation of ibroprofen (branched product) and 3-(4-isobutylphenyl)propionic acid (linear product) in a 98/2 ratio. The results of the GC analyses are shown in Table I.

Part D

Essentially repeat Part C except for using a 50/50 $Ph_3P/Ph_3PO$ mixture instead of the 85/15 mixture. The ibuprofen product has a branched/linear ratio of 100/0. The results of the GC analyses are shown in Table I.

Part E

Essentially repeat Part A except for replacing the triphenylphosphine with 0. 14 g (0.50 mmol) of $Ph_3P/Ph_3PS$ (50/50). The branched/linear ratio in the ibuprofen product is 100/0. Results of the GC analyses are shown in Table I.

Part F

Essentially repeat Part A except for replacing the triphenylphosphine with a mixture of 0.065 g (0.25 mmol) of $Ph_3P$ and 0.085 g (0.25 mmol) of $Ph_3PSe$. The branched/linear ratio in the ibuprofen product is ~200/1. Results of the GC analyses are shown in Table I.

TABLE I

Reaction Rates Using $Ph_3P$, $Ph_3PO$, $Ph_3P/Ph_3PO$, $Ph_3P/Ph_3PS$, or $Ph_3P/Ph_3PSe$

| | % Conversion to Product | | | | | |
|---|---|---|---|---|---|---|
| Hours | Ex. 1-A | Ex. 1-B | Ex. 1-C | Ex. 1-D | Ex. 1-E | Ex. 1-F |
| 2 | 3 | 0 | 8 | 34 | 21 | 8 |
| 3 | — | 0 | — | 50 | — | — |
| 4 | 9 | 0 | 17 | 60 | 41 | 12 |
| 5 | — | 0 | — | 69 | — | — |
| 6 | 11 | 0 | 24 | 77 | 53 | 21 |
| 8 | 16 | 0 | 32 | 89 | 65 | 26 |
| 10 | 19 | 0 | 40 | 95 | 76 | 31 |
| 22 | — | 0 | 77 | — | — | — |
| 23 | — | 0 | — | 100 | 97 | — |
| 24 | — | 0 | — | — | — | — |
| 46 | — | — | 98 | — | — | — |
| 70 | — | — | — | — | — | 73 |

EXAMPLE 2

Part A (Comparative)

Essentially repeat Example 1, Part A, except for replacing the triphenylphosphine with 0. 13 g (0.50 mmol) of $CyPh_2P$. The ibuprofen product has a branched/linear ratio of ~250/1. The results of the GC analyses are shown in Table II.

Part B

Essentially repeat Part A except for replacing the $CyPh_2P$ with 0.14 g (0.53 mmol) of $CyPh_2P/CyPh_2PO$ (85/15). The results of the GC analyses are shown in Table II.

Part C

Essentially repeat Part B except for using a 50/50 $CyPh_2P/CyPh_2PO$ mixture instead of the 85/15 mixture. The ibuprofen product has a branched/linear ratio of 100/0. The results of the GC analyses are shown in Table II.

TABLE II

Reaction Rates Using CyPh₂P or CyPh₂P/CyPh₂PO

| | % Conversion to Product | | |
|---|---|---|---|
| Hours | Ex. 2-A | Ex. 2-B | Ex. 2-C |
| 2 | 2 | 3 | 38 |
| 4 | 5 | 8 | 64 |
| 6 | 8 | 13 | 84 |
| 7 | — | — | 91 |
| 8 | 14 | 19 | 96 |
| 10 | 18 | 24 | 100 |
| 22 | — | 53 | — |
| 24 | 42 | — | — |
| 48 | 78 | — | — |

EXAMPLE 3

Part A (Comparative)

Essentially repeat Example 1, Part A, except for replacing the triphenylphosphine with 0.11 g (0.49 mmol) of EtPh₂P. No reaction occurs in 8 hours at 50° C. Raise the temperature to 90° C. and agitate while monitoring by GC. GC analyses show 59% conversion after 14 hours at the higher temperature and 79% conversion after 21 hours at that temperature. The ibuprofen product has a branched/linear ratio of 68/32.

Part B

Essentially repeat Part A except for using as the ligand a mixture of 0.053 g (0.25 mmol) of EtPh₂P and 0.057 g (0.25 mmol) of EtPh₂PO. As in Part A, no reaction occurs in 8 hours at 50° C., but complete conversion is achieved in only 14 hours at 90° C. The ibuprofen product has a branched/linear ratio of 88/12.

EXAMPLE 4

Part A (Comparative)

Essentially repeat Example I, Part A, except for replacing the 1 mL of water with 1 mL of 10% aqueous HCl. The ibuprofen product has a branched/linear ratio of 98/2. The results of the GC analyses are shown in Table III.

Part B

Essentially repeat Example I, Part D, except for replacing the 1 mL of water with 1 mL of 10% aqueous HCl. The ibuprofen product has a branched/linear ratio of 100/0. The results of the GC analyses are shown in Table III.

TABLE III

Reaction Rates Using Acid and Ph₃P or Ph₃P/Ph₃PO

| | % Conversion to Product | |
|---|---|---|
| Hours | Ex. 4-A | Ex. 4-B |
| 2 | 8 | 54 |
| 3 | — | 74 |
| 4 | 20 | 91 |
| 5 | — | 100 |
| 6 | 34 | — |

TABLE III-continued

Reaction Rates Using Acid and Ph₃P or Ph₃P/Ph₃PO

| | % Conversion to Product | |
|---|---|---|
| Hours | Ex. 4-A | Ex. 4-B |
| 8 | 45 | — |
| 10 | 56 | — |
| 20 | 100 | — |

EXAMPLE 5

Part A (Comparative)

Essentially repeat Example 4, Part A, except for also including 0.05 g (0.37 mmol) of CuCl₂ in the initial charge to the autoclave. The reaction results in the formation of ibuprofen containing no linear product. The results of the GC analyses are shown in Table IV.

Part B

Repeat Part A except for replacing the Ph₃P ligand with 0.14 g (0.51 mmol) of Ph₃P/Ph₃PO (85/15). As in Part A, the reaction results in the formation of ibuprofen containing no linear product. The results of the GC analyses are shown in Table IV.

TABLE IV

Reaction Rates Using Cu, Acid, and Ph₃P or Ph₃P/Ph₃PO

| | % Conversion to Product | |
|---|---|---|
| Hours | Ex. 5-A | Ex. 5-B |
| 2 | 36 | 48 |
| 4 | 72 | 88 |
| 5 | — | 100 |
| 6 | 100 | — |

EXAMPLE 6

Part A (Comparative)

Essentially repeat Example 1, Part A, except for replacing the water and THF with 1 mL of MeOH and 30 mL of MEK, respectively, and also including 0.05 g (0.37 mmol) of CuCl₂ in the initial charge to the autoclave. The reaction results in the formation of methyl 2-(4-isobutylphenyl)propionate (branched product) and methyl 3-(4-isobutylphenyl) propionate (linear product) in a 98/2 ratio. Results of the GC analyses are shown in Table V.

Part B

Essentially repeat Part A except for (1) not replacing the THF with MEK and (2) using, in addition to the triphenylphosphine, 0.14 g (0.49 mmol) of Ph₃PO. Table V shows the results of the GC analyses conducted up to the stage of 100% conversion to the ibuprofen ester product having a branched/linear ratio of ~200/1.

Cool the reactor to room temperature, release CO pressure, add 20 mL of water, and extract the product with hexane (3×50 mL). Dry the combined hexane extracts with MgSO₄, concentrate by rotary evaporation, and chromatograph the resulting residue on a short column (silica gel, eluted with hexanes and 5/1 hexanes/ethyl acetate) to give 1.56 g (89%) of a colorless liquid.

TABLE V

Reaction Rates Using Cu and Ph₃P or Ph₃P/Ph₃PO

| | % Conversion to Product | |
|---|---|---|
| Hours | Ex. 6-A | Ex. 6-B |
| 2 | 2 | 14 |
| 4 | 23 | 41 |
| 6 | 51 | 73 |
| 8 | 73 | 92 |
| 10 | — | 100 |
| 22 | 100 | — |

EXAMPLE 7

Part A (Comparative)

Essentially repeat Example 6, Part A, except for employing no CuCl₂ in the reaction. The ester product has a branched/linear ratio of 97/3. Results of the GC analyses are shown in Table VI.

Part B

Repeat Part A except for replacing the triphenylphosphine ligand with 0.13 g (0.50 mmol) of Ph₃P/Ph₃PO (50/50). The ester product has a branched/linear ratio of ~200/1. Results of the GC analyses are shown in Table VI.

TABLE VI

Reaction Rates Using Ph₃P or Ph₃P/Ph₃PO

| | % Conversion to Product | |
|---|---|---|
| Hours | Ex. 7-A | Ex. 7-B |
| 2 | 0 | 9 |
| 4 | 2 | 26 |
| 6 | 6 | 42 |
| 8 | 11 | 58 |
| 22 | 76 | — |
| 23 | — | 99 |

The preceding examples demonstrate the unexpected improvements in reaction rate and product branched/linear ratio attained when mixtures of $R_3ZY$ and $R'_3Z$ ligands are used in the acid and ester syntheses instead of conventional single ligands. The following example shows that similar results are observed when the $R_3ZY$ and $R'_3Z$ ligand elements of the novel mixtures are present in a single compound.

EXAMPLE 8

Part A (Comparative)

Essentially repeat Example 1, Part A, except for replacing the triphenylphosphine with 0.075 g (0.17 mmol) of 1,3-bis(diphenylphosphino)propane. No reaction occurs in 21 hours at 50° C. Raise the temperature to 80° C. and agitate while monitoring by GC. The product branched/linear ratio is 32/68. Results of the GC analyses are shown in Table VII.

Part B

Essentially repeat Example 1, Part A, except for replacing the triphenylphosphine with 0.077 g (0.18 mmol) of 1,3-bis(diphenylphosphino)propane monoxide. The branched/linear ratio is 100/0. Results of the GC analyses are shown in Table VII.

Part C

Essentially repeat Part B except for conducting the reaction at 80° C. instead of 50° C. The branched/linear ratio is 98/2. Results of the GC analyses are shown in Table VII.

TABLE VII

Reaction Rates Using 1,3-bis(diphenylphosphino)propane or 1,3-bis(diphenylphosphino)propane monoxide

| | % Conversion to Product | | |
|---|---|---|---|
| Hours | Ex. 8-A[1] | Ex. 8-B[2] | Ex. 8-C[1] |
| 2 | 12 | 7 | 78 |
| 3 | 16 | — | 92 |
| 4 | 20 | 13 | 95 |
| 6 | 25 | 22 | 98 |
| 8 | — | 27 | — |
| 9 | 30 | — | — |
| 10 | — | 34 | — |
| 23 | — | 68 | — |

[1]Reaction at 80° C.
[2]Reaction at 50° C.

I claim:

1. A process for preparing an aralkanoic acid corresponding to the formula $CH(R^3)(R^4)$—$C(R^2)(Ar)$—$COOH$ by reacting an aralkene having the formula $C(R^3)(R^4)$=$C$—$(R^2)Ar$ with water and carbon monoxide at a temperature of 25–200° C. and a pressure of at least 1 atmosphere (0.1 MPa) in the absence of oxygen and in the presence of a palladium catalyst mixture containing a ligand; characterized in that the ligand comprises a combination of $R_3ZY$ and $R'_3Z$ ligand elements;

each R and R' in the above formulas being (a) independently selected from alkyl, aryl, and substituted aryl groups or (b) joined with the other Rs and R's and the Z in the same formula to form a heteroaromatic ring; Y representing oxygen, sulfur, or selenium; Z represents an element having a pauling electronegativity of 1.9–2.5; $R^2$, $R^3$, and $R^4$ being independently selected from hydrogen, alkyl, halo, trifluoromethyl, alkoxy, alkylthio, alkanoyl, cycloalkylsubstituted alkyl, cycloalkyl, substituted or unsubstituted aryl or heteroaryl, and substituted or unsubstituted aroyl or heteroarylcarbonyl groups; and Ar being substituted or unsubstituted aryl.

2. The process of claim 1 wherein the palladium catalyst mixture comprises palladium(0) and/or one or more salts of palladium, optionally in conjunction with one or more copper salts, in addition to the combination of $R_3ZY$ and $R'_3Z$ ligand elements.

3. The process of claim 1 wherein the combination of $R_3ZY$ and $R'_3Z$ ligand elements is provided by separate $R_3ZY$ and $R'_3Z$ ligands.

4. The process of claim 3 wherein the $R_3ZY$ and $R'_3Z$ ligands are triphenylphosphine oxide and triphenylphosphine.

5. The process of claim 1 wherein the combination of $R_3ZY$ and $R'_3Z$ ligand elements is provided in a single ligand.

6. The process of claim 1 conducted in a reaction medium.

7. The process of claim 6 wherein the reaction medium is tetrahydrofuran.

8. The process of claim 6 wherein the reaction medium is methyl ethyl ketone.

9. The process of claim 1 wherein an aralkene selected from 4-isobutylstyrene and 2-methoxy-6-vinylnaphthalene is reacted with carbon monoxide and water in the presence of a palladium catalyst mixture comprising a palladium salt, a mixture of triphenylphosphine and triphenylphosphine oxide ligands, and optionally also a copper salt.

* * * * *